United States Patent [19]

Sholl et al.

[11] 4,222,275
[45] Sep. 16, 1980

[54] SYSTEM FOR NON-DESTRUCTIVELY ACQUIRING AND PROCESSING INFORMATION ABOUT A TEST PIECE

[75] Inventors: Howard A. Sholl, Storrs; John T. Marshall, Willimantic, both of Conn.

[73] Assignee: Dapco Industries, Inc., Ridgefield, Conn.

[21] Appl. No.: 947,481

[22] Filed: Oct. 2, 1978

Related U.S. Application Data

[63] Continuation-in-part of Ser. No. 946,942, Sep. 29, 1978.

[51] Int. Cl.$^2$ ............................................. G01N 29/04
[52] U.S. Cl. .......................................... 73/636; 73/639
[58] Field of Search ........................... 73/636, 639, 625

[56] References Cited

U.S. PATENT DOCUMENTS

| | | | |
|---|---|---|---|
| 4,102,204 | 7/1978 | Kretz | 73/639 |
| 4,165,648 | 8/1979 | Pagano | 73/625 |

*Primary Examiner*—Anthony V. Ciarlante
*Attorney, Agent, or Firm*—St. Onge, Steward, Johnston, Reens & Noe

[57] ABSTRACT

A system for non-destructively acquiring and processing information about a test piece includes an array of ultrasonic transducers each adapted to transmit ultrasonic energy into the test piece and to receive ultrasonic energy transmitted back thereto to produce a response signal capable of representing deviation from the expected condition of the test piece. The transducers are mounted on a carriage to be transported relative to the test piece and a transducer control sequentially pulses the transducers while so transported to ultrasonically inspect the test piece and produce a set of response signals representing the inspection. A plurality of transducer monitors, one for each transducer, sequentially monitor each of the response signals and an analogue-to-digital converter converts each monitored response signal to a single set of digital data. A digital preprocessing subsystem compresses each single set of digital data for subsequent processing by the system and includes a digital peak detector for identifying the subset of data in each single set of data having maximum points of inflection. A threshold datum generator produces a digital threshold datum representative of acceptable background noise characteristic of each of the response signals. A digital threshold computer compares the maximum data and the threshold datum and a digital multiplexor transmits only the maximum data of each single set of data that is greater than the threshold datum to a memory for subsequent processing by the system.

9 Claims, 8 Drawing Figures

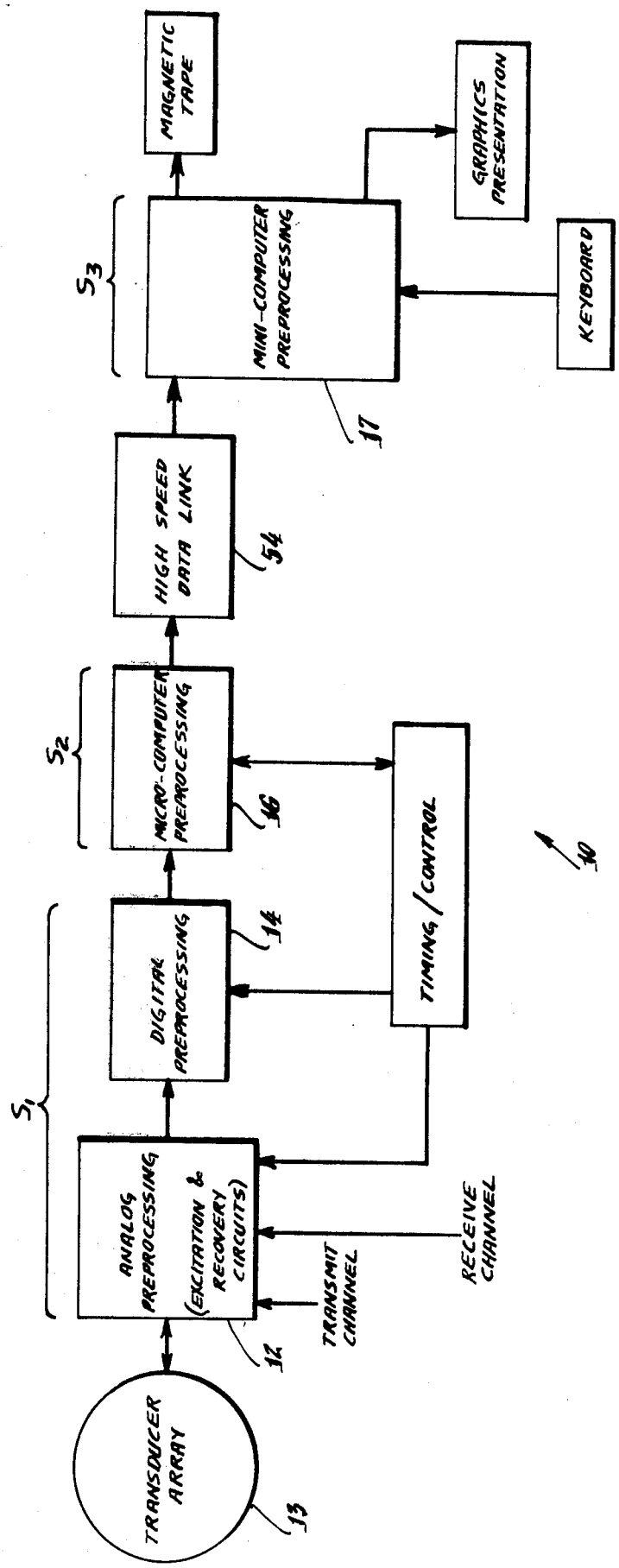

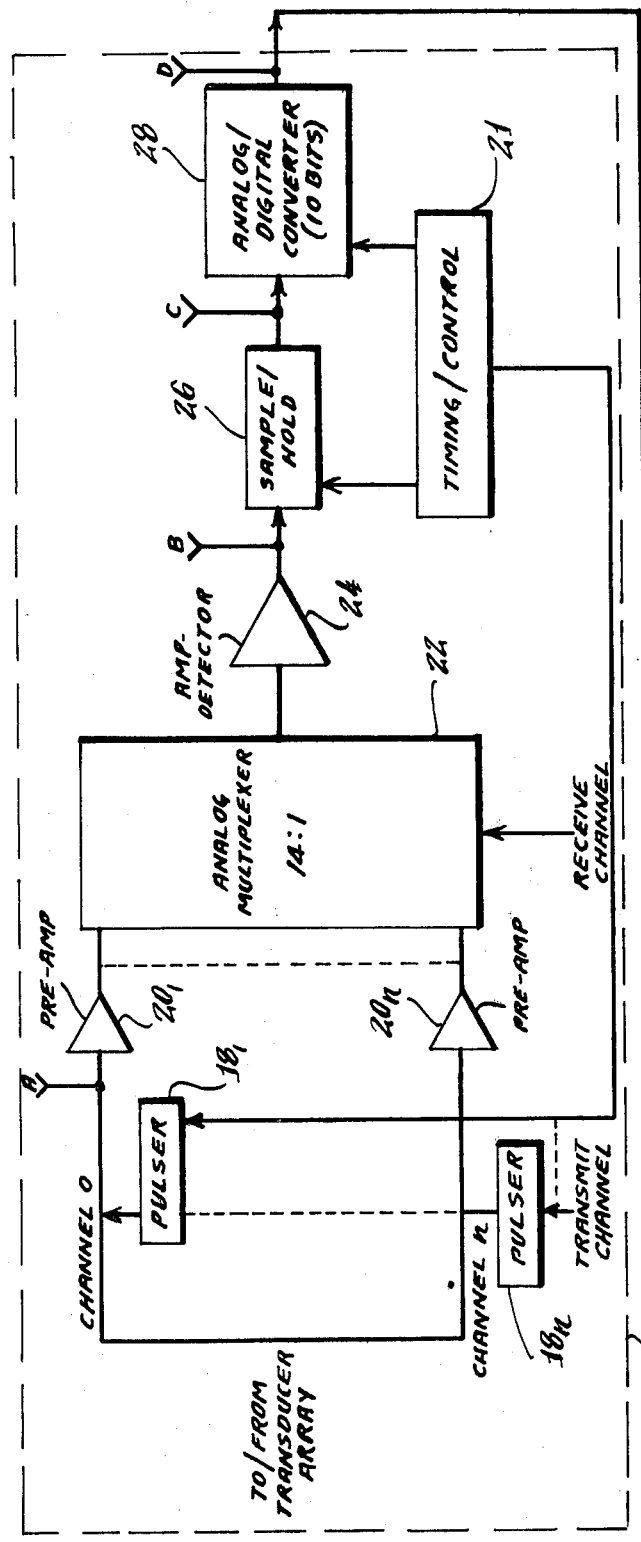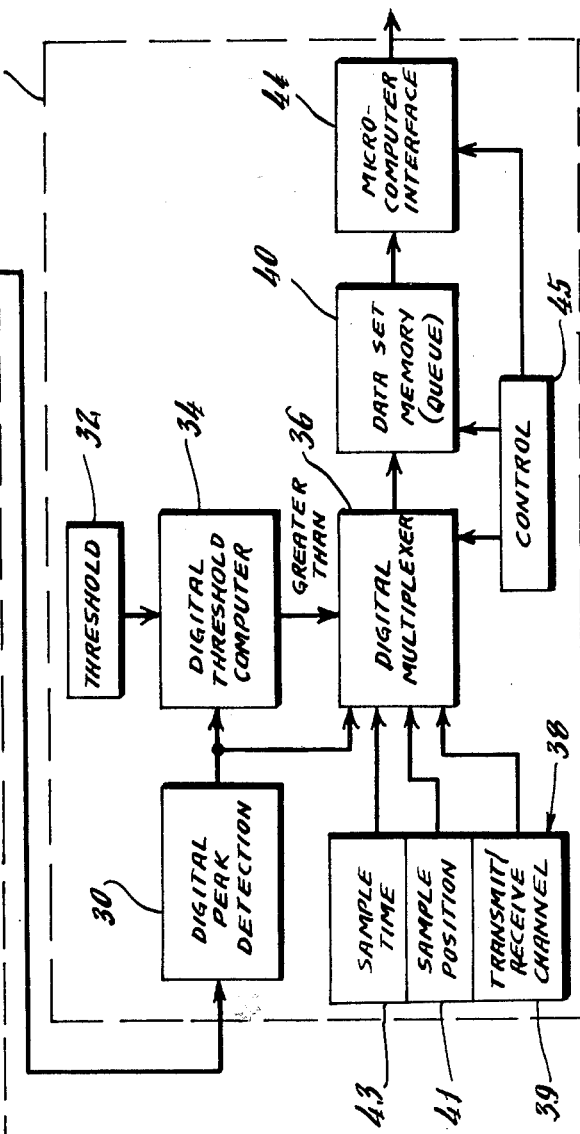

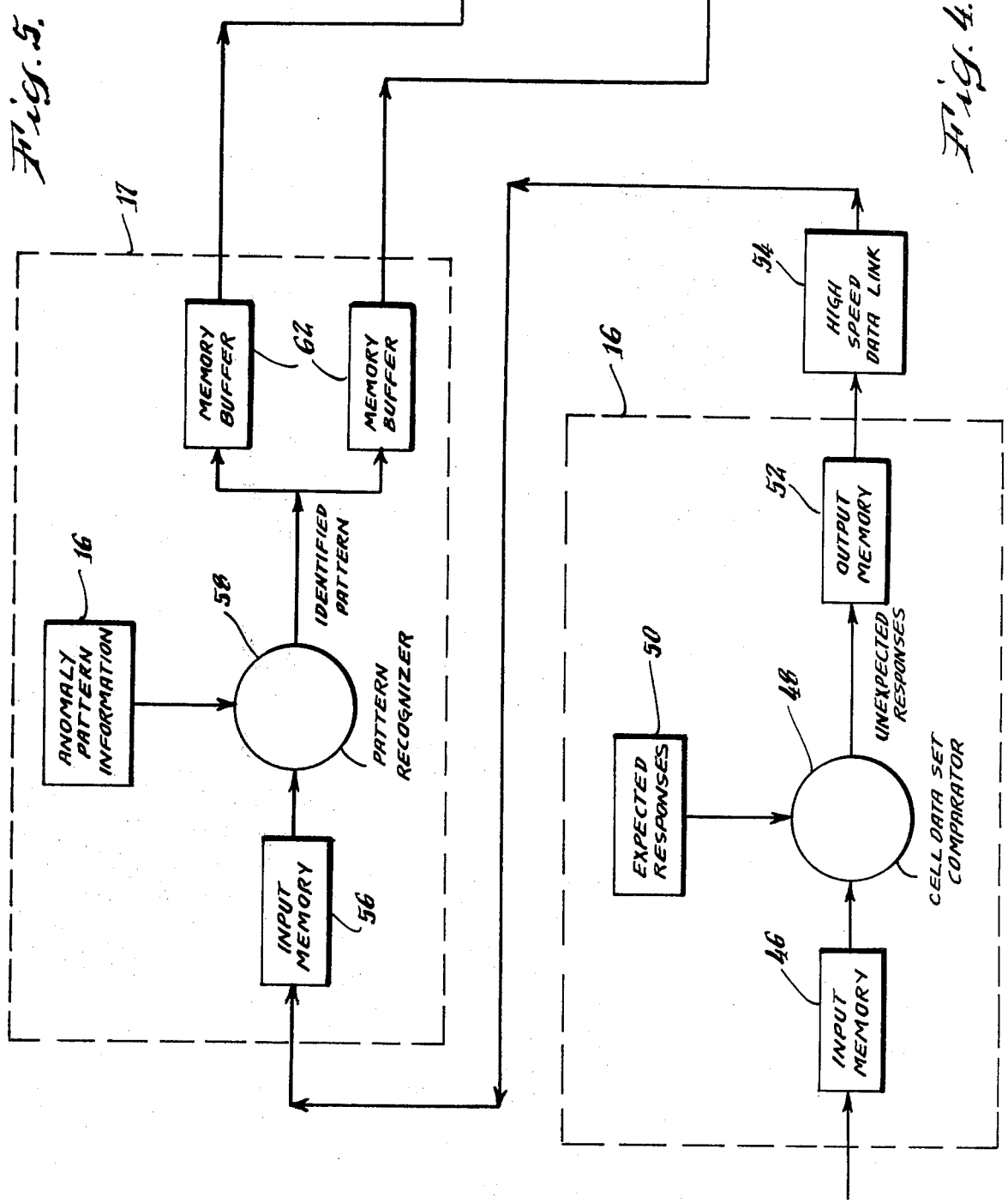

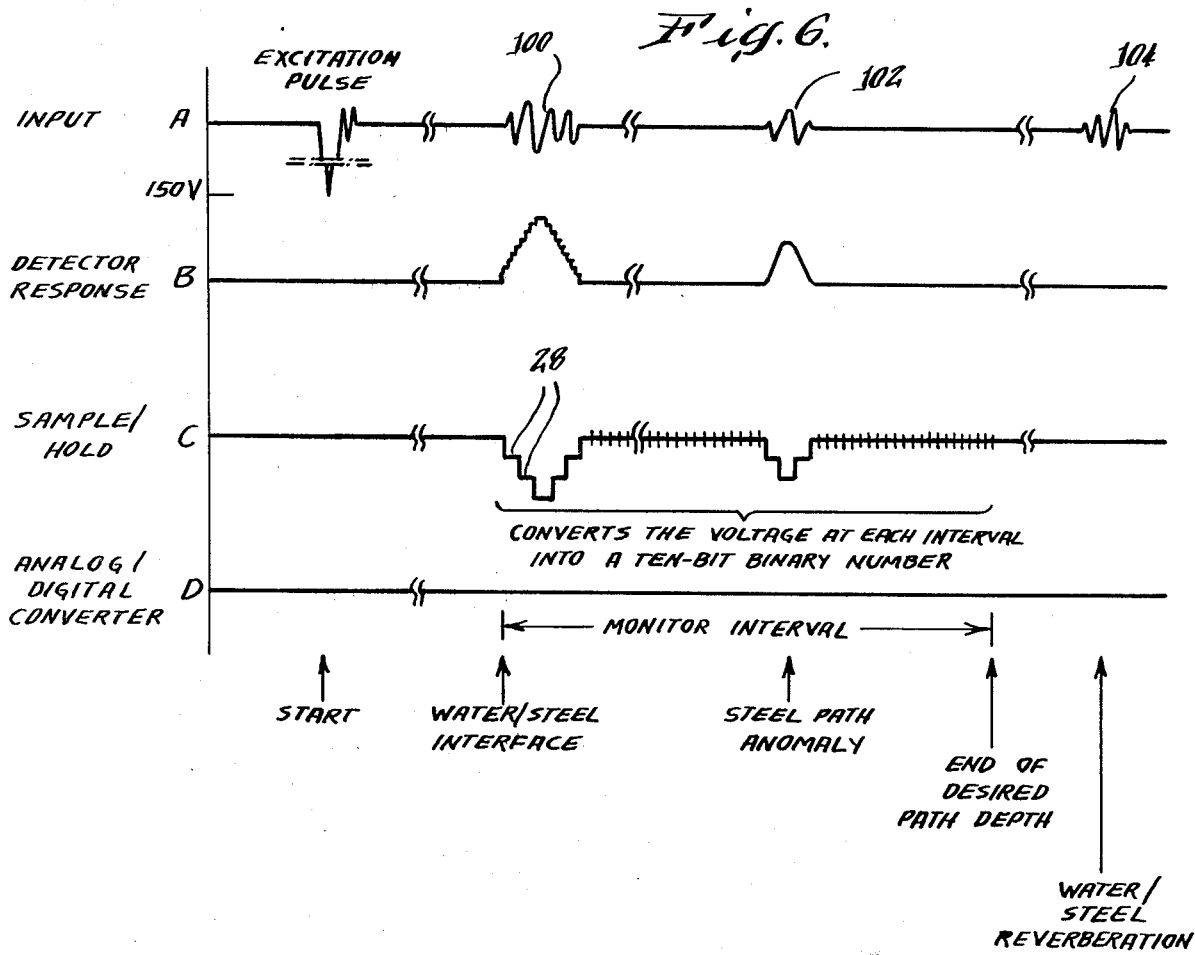
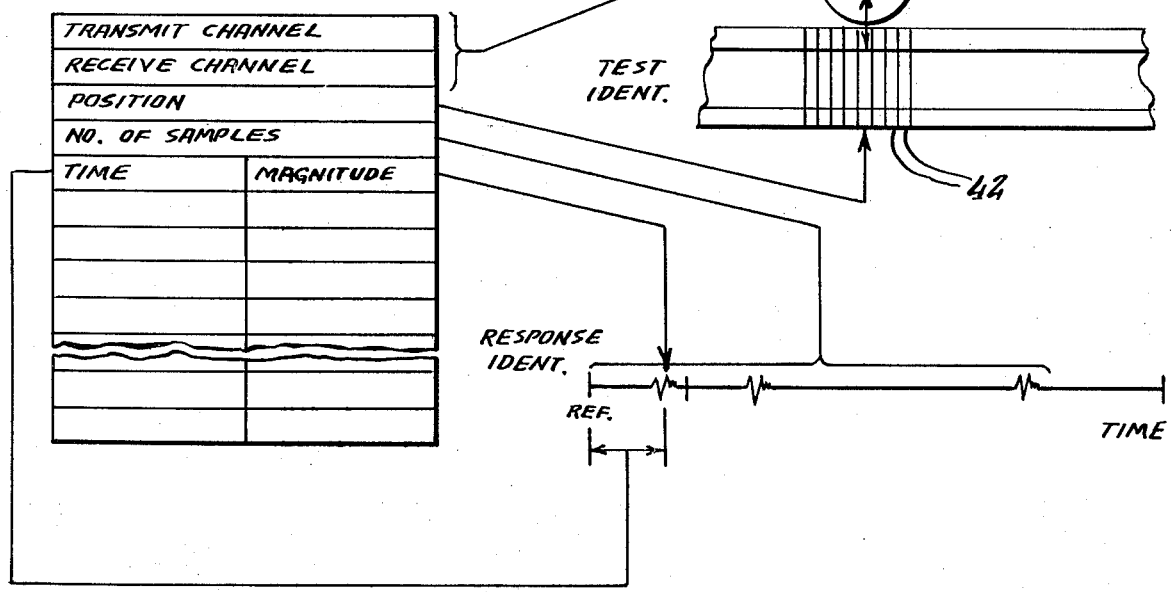

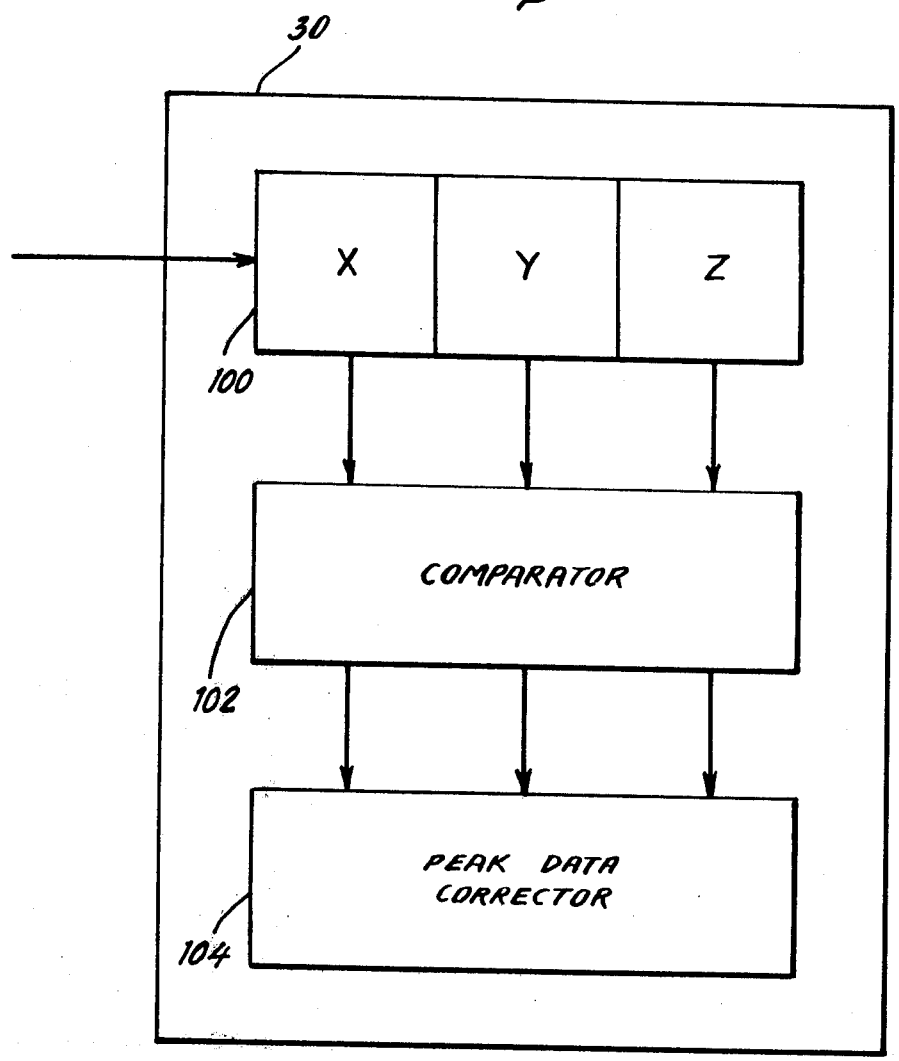

SYSTEM FOR NON-DESTRUCTIVELY ACQUIRING AND PROCESSING INFORMATION ABOUT A TEST PIECE

This application is a continuation-in-part of U.S. Patent Application Ser. No. 946,942, filed Sept. 29, 1978 for a "System for Non-Destructively Acquiring and Processing Information About a Test Piece.

BACKGROUND OF THE INVENTION

The present invention relates to a system for non-destructively acquiring and processing information about a test piece in real time. The system has particular application in non-destructive ultrasonic inspection of test pieces such as railroad rails. However, the system may be used to acquire and process information in real time derived from arrays of ultrasonic transducers designed to inspect other types of test pieces.

Various systems for ultrasonically inspecting test pieces are presently known. Such a system for testing a railroad rail is disclosed in U.S. Pat. No. 4,165,648 (Pagano) and includes leading and trailing ultrasonic inspection wheels adapted to roll on a railroad rail in spaced relation. An array of ultrasonic transducers is mounted in each inspection wheel and includes two transducers looking laterally of the rail, three transducers looking longitudinally, one transducer looking normally and one send/receiver transducer. The send/receive transducer in the leading wheel operates in cooperation with the similar transducer in the trailing wheel to transmit ultrasonic energy thereto and receive ultrasonic energy therefrom in an alternating send/receive mode. Each of the transducers in the leading and trailing wheels is independently capable of transmitting ultrasonic energy, through a suitable coupling medium in the wheel, into the rail and of receiving ultrasonic energy transmitted back thereto to produce an individual response signal. Each response signal is capable of indicating anomolies in the rail, be they expected or unexpected, by indicating if ultrasonic energy has been deflected away from or attenuated in transit to an energy receiving transducer. Expected rail anomolies include joints in welded rails and bolt holes. Unexpected anomolies in rails include vertical split head and bolt hole enlargement defects. The type of anomoly detected may be classified at least in part by noting the transducers in the array which produced and received the energy indicating the anomoly. For example, vertical split head and rail defects are detected by energy produced and received by the laterally looking transducers in the apparatus described above.

While the wheels are rolled along the rail, the transducers are energized or pulsed in a known sequence selected to minimize interference from other transducers operative in the system and are subsequently monitored, also in a known sequence, to produce a set of response signals representing the ultrasonic inspection of the rail. It is apparent, then, that the transducer arrays produce a large volume of information in short periods of time, particularly when the inspection wheels are moved rapidly over the rail.

It is desirable to process and classify the large volume of information derived from such rail inspection apparatus in real time, that is, as the information is being collected or acquired. However, in the past, problems have been encountered in designing support systems for acquiring and analyzing information with the desired rapidity. One limiting factor, which in the past has prevented real time processing and analysis, is the time required for the system to make an information classification decision. The rate at which information is collected and, hence, the desired information input rate is not compatible with the rate at which the support system can process the information. Furthermore, simply too much information may be produced for the support system to digest. Therefore, two stage classification processes have been developed wherein information is collected in a first stage and classified and analyzed in non-real time in a second stage. However, such two-stage systems have disadvantages.

SUMMARY OF THE INVENTION

It is an object of the present invention to provide a system for acquiring and processing information about a test piece, such as a railroad rail, from an inspection apparatus comprising an array of ultrasonic transducers while the array is operated to inspect the test piece, that is, in real time.

It is a further object of the present invention to provide a subsystem, forming part of the system, that compresses the information acquired and subsequently required to be analyzed in order to enhance the capability of the system to acquire and process information in real time.

In its preferred embodiment, the system of the present invention is of the pipeline distributed processing type and includes an array of ultrasonic transducers each adapted to transmit ultrasonic energy into a test piece and to receive ultrasonic energy transmitted back thereto to produce a response signal capable of representing deviation from the expected condition of the test piece. The array of transducers is mounted on a carriage to be transported relative to and ultrasonically coupled to the test piece. While so transported, each transducer in the array is sequentially energized or pulsed by a pulse control to ultrasonically inspect the test piece, the array thereby producing a set of response signals representing the inspection. Each of a plurality of monitors receives the response signal produced by one transducer and an analogue-to-digital converter converts each monitored response signal to a signal set of digital data.

The improved subsystem of the invention, which enhances the ability of the system to process data in real time, compresses each single set of digital data for subsequent processing by the system and comprises a digital peak detector for identifying the subset of data in each single set of data having maximum points of inflection. A threshold datum generator produces a digital threshold datum representative of acceptable background noise characteristic of each response signal. A digital threshold computer compares the maximum data and the threshold datum and a digital multiplexer transmits only maximum data of each single set of datum which is greater than the threshold datum to a memory for subsequent processing by the system.

Accordingly, the subsystem of the present invention discards all but the maximum data in each single set of data. Moreover, if each set of data has no data greater than the threshold indicative of acceptable background noise, the entire set of data is discarded. Therefore, only useful data which need be processed to identify deviation from the expected condition of the test piece is retained. Accordingly, the real time data processing capability of the system of the invention is greatly enhanced.

The subsystem of the present invention also includes a multiplexer for multiplexing, to the memory, each maximum data with other data representative of the transducer transmitting ultrasonic energy which resulted in the maximum data, the transducer receiving the ultrasonic energy and generating the response signal resulting in the maximum data, the position of the transducer array relative to the test piece when the response signal resulting in the maximum data was produced, and the time after initiation of the inspection at which the maximum data was produced. Accordingly, any anomoly and particularly any deviation from the expected condition of the test piece can be precisely located and classified.

Other objects, aspects, and advantages of the present invention will be pointed out in or will be understood from the following detailed description provided below in conjunction with the accompanying drawings.

BRIEF DESCRIPTION OF THE DRAWINGS

FIG. 1 is a diagrammatic representation of the system of the present invention for non-destructively acquiring and processing information about a test piece.

FIG. 2 is a diagrammatic representation of an analogue preprocessing subsystem of the present invention.

FIG. 3 is a diagrammatic representation of a digital preprocessing subsystem of the system of the present invention for compressing data in accordance therewith.

FIG. 4 is a diagrammatic representation of microcomputer preprocessing subsystem of the system of the invention.

FIG. 5 is a diagrammatic representation of minicomputer signal processing subsystem yielding the final output of the system.

FIG. 6 is a graph illustrating the transducer response signal description at various stages of information processing.

FIG. 7 is a description of the total data set assembled by the digital preprocessing subsystem of the present invention.

FIG. 8 is a detailed diagrammatic representation of the digital peak detector forming a part of the digital preprocessing subsystem of the present invention.

DETAILED DESCRIPTION OF THE PREFERRED EMBODIMENT

The system for acquiring and processing information acquired by ultrasonic inspection of a test piece of the present invention is shown generally in FIG. 1. This system is of the pipeline distributed processing type and is intended to accurately perform high speed real time pattern recognition tasks. The system comprises three basic stages. In the first $S_1$, information is acquired, filtered and converted from analogue to digital form. In the second $S_2$, which is microcomputer based, features of the test piece which deviate from the expected condition of the test piece are extracted and detected. In the third stage $S_3$, the extracted features deviating from the expected test piece condition are classified in accordance with known non-expected condition patterns and are filed for storage or are displayed.

This system may be utilized to perform many different pattern recognition tasks. However, for convenience of description, it will be described with reference to high speed inspection of a railroad rail performed by ultrasonic inspection apparatus described in U.S. Pat. No. 4,164,648 (Pagano) which is incorporated herein by reference.

As shown in FIG. 1, the first stage $S_1$ of the system of the present invention, generally indicated at 10, comprises an analogue preprocessing subsystem 12 for operating the inspection apparatus and preprocessing the analogue data received from the transducer array 13 of the inspection apparatus. The first stage $S_1$ further includes a digital preprocessing subsystem 14 which compresses data that has been converted to digital form for subsequent processing by the system to enhance its real time data processing capabilities. It is this digital subsystem which is of particular importance to the present invention.

The second stage $S_2$ of the system comprises a microcomputer preprocessing subsystem 16 that identifies those features of the test piece, now represented by digital data stored in the digital preprocessing subsystem 14 which deviate from expected features of the test piece.

The third stage $S_3$ of the system comprises a minicomputer signal preprocessing subsystem 17 that receives the data representative of features deviating from the expected condition of the test piece and compares this data with data representative of known anomolous features. As noted above, such known anomolies in railroad rails include vertical split head defects, rail web defects, bolt hole breaks and bolt hole enlargement.

FIG. 2 illustrates in detail the analogue preprocessing subsystem 12 forming one part of the first stage $S_1$ of the system of the present invention. This subsystem comprises a plurality of pulsers $18_1$-$18_n$, n being equal to the number of transducers in the inspection apparatus. As noted above, the rail inspection apparatus includes fourteen transducers. Each pulser is coupled to one transducer to energize or pulse it. Further, the pulsers are controlled by a timing/control 21 to energize the transducers in a predetermined sequence selected to minimize crosstalk or interference between transducers, that is, to minimize the signal-to-noise ratio of the inspection apparatus.

Each of a plurality of preamplifiers $20_1$-$20_n$ is connected to one transducer to monitor or receive and balance the response signal produced thereby. An analogue multiplexer 22 is connected to each preamplifier and multiplexes the transducer response signals received thereby to an amplifier detector 24, also in a predetermined sequence. This multiplexing sequence may be the same as or different from the sequence in which the pulsers 18 energize the transducers. The amplifier-detector 24 linearly or logarithmically amplifies and envelope-detects the response signal from each respective transducer.

A sample and hold component 26 sequentially receives each amplified response signal and estimates it, in the preferred embodiment, in 1.25 microsecond intervals. That is, each response signal is sampled at discrete sample intervals of 1.25 microseconds to yield a digitized output.

The digitized response signal is then fed to an analogue-to-digital converter 28 where it is converted to a set of digital data, in the preferred embodiment, of 10 bits at 800 kHz frequency.

FIG. 6 illustrates the analogue signal description at each stage of the analogue preprocessing in subsystem 12 as a function of time. Line A illustrates a typical transducer response signal as it would appear at location A of FIG. 2 on the line between a transducer and an associated preamplifier. The response signal comprises an analogue excitation impulse and a sequence wave forms, the first wave form 100 of which indicates an expected response as the ultrasonic energy passes through the interface from the inspection apparatus into the test piece. The second wave form 102 represents an unexpected response that deviates from the expected condition of the test piece. The third wave form 104 represents reverberation at the interface of the test piece and apparatus when the ultrasonic energy passes back therethrough.

Line B illustrates the response signal shown on line A as it is output from the amplifier-detector 24 at location B in FIG. 1. Averaging of the response signal in the sample and hold component 26 appears as line C wherein each wave form is averaged over discrete sample intervals 28. The first wave form 100 of the response signal has duration producing five such sample intervals. The wave form 102 indicating deviation from the expected test piece condition has duration producing three sample intervals. The line C occurs at location C of FIG. 2. Line D represents the set of digital data representative of the typical analogue response signal shown on lines A, B and C as it is output from the analogue to digital converter 28.

The digital preprocessing subsystem 14 designed in accordance with the present invention is shown in FIG. 3. This subsystem compresses the digital data from the analogue-to-digital converter to enhance capability of the system 10 to process data in real time. The digital preprocessing subsystem comprises a digital peak detector 30 which detects the peak or maximum data in each set of digital data conducted thereto. That is, the digital detector identifies the subset of data in each set of digital data having maximum points of inflection. Once the maximum data, that is, the subset of data having maximum points of inflection, in each set of data are detected, the peak detector discards all other data from that set. Accordingly, significant compression of data is achieved. For example, in the wave form 102 having duration requiring three sample intervals, data representing two of the three sample intervals is discarded, only one being retained.

The digital preprocessing subsystem further comprises a digital threshold datum generator 32 that generates a threshold datum indicative of the acceptable of baseline noise characteristic of the ultrasonic transducers of the inspection apparatus. The digital peak detector 30 and digital threshold datum generator 32 are each connected to a digital threshold computer 34 that compares the maximum data and the threshold data. If the maximum datum is greater than the threshold datum, it is conducted to a digital multiplexer 36. If not, it is discarded.

In addition to being connected to the digital threshold computer, the digital multiplexer 36 is also connected to a classification and location data generator 38 that produces data to be multiplexed with each maximum data for locating and classifying anomolies deviating from the expected condition of the test piece. This data generator 38 includes a portion 39 for generating a set of receiving channel data, each datum of which represents the one of the transducers producing each one of the response signals from which the associated maximum data may be derived. That is, each receiving channel datum identifies the transducer receiving ultrasonic energy and generating a response signal from which a specific maximum data may be derived.

The portion 39 of the data generator further generates a set of transmitting channel data, each datum of which represents the one of the transducers that was pulsed or energized to produce each one of the response signals from which an associated maximum data may be derived. That is, the transducer generating ultrasonic energy which resulted in the response signal from which the associated maximum data is derived is identified by this portion.

A portion 41 of the data generator 38 produces a set of location or position data, each datum of which represents the location of the transducer array relative to the test piece when the associated maximum data is generated. Specifically, each location datum indicates the location or cell of the test piece inspection of which is represented by an associated maximum data.

A portion 43 of the data generator 38 produces a set of time data, each datum of which represents the time after initiation of the inspection of the test piece when each maximum data is derived. Each transmitting channel datum, receiving channel datum, position datum, and time data, and the associated maximum datum, are multiplexed by the digital multiplexer 36 to a data set memory 40 from which the analysis of the maximum data may be performed. Each data set is representative of the response from one transducer.

FIG. 7 shows a completed data set derived from one response signal as it is multiplexed to memory 40. Further, as shown there schematically, the rail may be divided into a plurality of vertical columns or cells 42, each of which is to be inspected. Because the rail inspection apparatus comprises fourteen transducers that probe each cell from various directions, all transducers must pass over the cell before thorough probing is completed.

The stored data set shown in FIG. 7 representative of each transducer response signal is conducted through suitable microcomputer interface 44 to an input memory 46 of the microcomputer signal processing system 16, under the management of a microcomputer control 45. Each set of data representing inspection of one rail cell by all transducers, or each cell data set, is compared in a cell data set comparator 48 with an expected cell response data set generated by an expected cell response data generator 50. If the cell data set matches the expected cell response data set, the computer discards the information. However, if an unexpected response is indicated, the microcomputer forwards this information, in essence filtered cell data sets, to an output memory 52. The filtered cell data sets are transferred by a high speed data link 54 to the third or feature classification stage S₃ of the system of the invention. There, each filtered cell data set, indicating unexpected responses, is placed in an input memory 56. There, all data sets representing complete probing of each rail cell 42 are amalgamated as a cell data set before further data processing. The filtered cell data sets are then compared in a pattern recognizer 58 with a set of non-expected cell data sets provided by a pattern generator 60. Each non-expected cell data set represents one test piece anomoly, such as in the case of rail testing, a vertical split head defect. The identified pattern is then conducted to a memory buffer 62 for display as a graphic display 64 or for storage on a magnetic tape 66 for subsequent use.

The digital peak detector 30 is illustrated in greater detail in FIG. 8 and comprises a three-stage shift register 100, a comparator 102 and a peak data corrector 104. Each digital subset of data is shifted through stages X, Y and Z of register 100 and between shifting operations, the subset of data in stage Y is compared with those subsets in stages X and Z by comparator 102. This comparison occurs continuously as subsets are shifted through the register. If these subsets in stage Y are greater than (or equal to) both subsets in stages X and Z, a peak is defined and all subsets are input to the peak data corrector. A correction is performed on the peak subset based on a known correction function of the adjacent subsets in stages X and Z. The corrected data subset is then input to the digital threshold computer 34 for further processing as described above.

If subset of data in stage Y is not greater than or equal to both subsets in stages X and Z, the subset in stage Z is discarded. In this way, the data compression function of the peak detector is enhanced.

It will be appreciated that the system of the present invention provides a pipeline distributed system for analyzing ultrasonic data in real time. This is possible because data processing in each of the three stages is performed on one data set while processing is performed in other stages on different data sets. It will further be appreciated that the digital preprocessing subsection 14 enhances the real time capability by compressing the data necessary to be processed.

Accordingly, although a specific embodiment of the present invention has been described above in detail, it is to be understood that this is only for purposes of illustration. Modifications may be made to the described system by those skilled in the art in order to adapt it to specific testing applications.

What is claimed is:

1. In a system for non-destructively acquiring and processing information about a test piece, including an array of ultrasonic transducers each adapted to transmit ultrasonic energy into the test piece and to receive ultrasonic energy transmitted back thereto to produce a response signal capable of representing deviation from the expected condition of the test piece, means for transporting said array relative to said test piece, means for sequentially pulsing said transducers while transported relative to the test piece to ultrasonically inspect said test piece and produce a set of said response signals representing the inspection, means of sequentially monitoring each of said response signals, and means for converting each said monitored response signal to a single set of digital data; the improvement comprising improved means for compressing each said single set of digital data for subsequent processing by said system, said improvement comprising:
 a digital peak detector, for identifying the subset of data in each said single set of data having maximum points of inflection, comprising a shift register having first, second and third stages for sequentially receiving and storing each subset of each said single set of data, and a subset comparator for determining when the subset of data stored in said second stage is greater than or equal to the subsets of data stored in said first and third stages and therefore has maximum points of inflection,
 means for generating a digital threshold datum representative of acceptable background noise characteristic of each said response signal,
 means for receiving said subsets of data having maximum points of inflection from said subset comparator and for then comparing said subsets of data having maximum points of inflection and said threshold datum; and
 means for storing only said subsets of data of said single sets of data which are greater than said threshold datum, for subsequent processing by said system.

2. The system for acquiring and processing information about a test piece as claimed in claim 1 further comprising data correcting means for correcting said subset of data stored in said second register when greater than or equal to said subsets stored in said first and third stages as a function of said subsets stored in said first and third stages.

3. In a system for non-destructively acquiring and processing information about a test piece, including an array of ultrasonic transducers each adapted to transmit ultrasonic energy into the test piece and to receive ultrasonic energy transmitted back thereto to produce a response signal capable of representing deviation from the expected condition of the test piece, means for transporting said array relative to said test piece, means for sequentially pulsing said transducers while transported relative to the test piece to ultrasonically inspect said test piece and produce a set of said response signals representing the inspection, means for sequentially monitoring each of said response signals, and means for converting each said monitored response signal to a single set of digital data; the improvement comprising improved means for compressing each said single set of digital data for subsequent processing by said system, said improvement comprising:
 means for identifying the subset of data in each said single set of data having maximum points of inflection,
 means for generating a digital threshold datum representative of acceptable background noise characteristic of each said response signal,
 means for comparing said subsets of data having maximum points of inflection and said threshold datum; and
 means for storing only said subsets of data of said single sets of data which are greater than said threshold datum, for subsequent processing by said system.

4. The system for acquiring and processing information about a test piece as claimed in claim 3 wherein said means for identifying the subset of data having maximum points of inflection comprises a digital peak detector.

5. The system for acquiring and processing information about a test piece as claimed in claim 3, further comprising:
 means for producing a set of receiving channel data, each datum of which represents the one of said transducers producing each one of said response signals from which an associated one of said subsets of data having maximum points of inflection may be derived; and
 means for multiplexing to said storing means, each datum of said receiving channel data and said associated one of said subsets of data.

6. The system for acquiring and processing information about a test piece as claimed in claim 3, further comprising:
 means for generating a set of transmitting channel data, each datum of which represents the one of said transducers that was pulsed to produce each one of said response signals from which an associated one of said subsets of data having maximum points of inflection may be derived; and means for multiplexing to said storing means, each datum of said transmitting channel data and said associated one of said subsets of data.

7. The system for acquiring and processing information about a test piece as claimed in claim 3, further comprising:

means for generating a set of position data, each datum of which represents the position of said array relative to said test piece at which one of said response signals, from which an associated one of said subsets of data having maximum points of inflection may be derived, is generated; and means for multiplexing to said storing means, each datum of said position data and said associated one of said subsets of data.

8. The system for acquiring and processing information about a test piece as claimed in claim 3, further comprising:

means for generating a set of time data, each datum of which represents the time after initiation of the inspection at which one of said response signals, from which an associated one of said subsets of data having maximum points of inflection may be derived, is generated; and means for multiplexing to said storing means, each datum of said time data and said associated one of said subsets of data.

9. In a system for non-destructively acquiring and processing information about a test piece, including an array of ultrasonic transducers each adapted to transmit ultrasonic energy into the test piece and to receive ultrasonic energy transmitted back thereto to produce a response signal capable of representing deviation from the expected condition of the test piece, means for transporting said array relative to said test piece, means for sequentially pulsing said transducers while transported relative to the test piece to ultrasonically inspect said test piece and produce a set of said response signals representing the inspection, means for sequentially monitoring each of said response signals and means for converting each of said monitored response signals to a single set of digital data; the improvement comprising means for compressing each said single set of digital data and for assembling it with the other associated data for subsequent processing by said system, said improvement comprising:

means for identifying the subset of data in each said single set of data having maximum points of inflection, means for generating a digital threshold datum representative of acceptable background noise characteristic of said response signal, means for comparing said subsets of data having maximum points of inflection and said threshold datum, means for storing only said subsets of data which are greater than said threshold datum, means for generating a set of receiving channel data, each datum of which represents the one of said transducers producing each one of said response signals from which an associated one of said subsets of data may be derived, means for generating a set of transmitting channel data, each datum of which represents the one of said transducers that was pulsed to produce each one of said response signals from which said associated one of said subsets of data may be derived, means for generating a set of position data, each datum of which represents the position of said array relative to said test piece at which one of said response signals, from which said associated one of said subsets of data may be derived, is generated, means for generating a set of time data, each datum of which represents the time after initiation of the inspection at which one of said response signals, from said associated one of said subsets of data may be derived is generated; and means for multiplexing, to said storing means, each datum of said receiving channel data, each datum of said transmitting channel data, each datum of said position data, each datum of said time data, and said associated one of said subsets of data.

* * * * *

UNITED STATES PATENT AND TRADEMARK OFFICE
CERTIFICATE OF CORRECTION

PATENT NO. : 4,222,275
DATED : 9/16/80
INVENTOR(S) : Howard A. Sholl and John T. Marshall It is certified that error appears in the above–identified patent and that said Letters Patent are hereby corrected as shown below:

Column 4, line 2, "4,164,648" should be -- 4,165,648 --.

Column 5, line 53, "threshold data" should be -- threshold datum --.

Column 5, line 54, "maximum datum" should be --maximum data --.

Column 6, line 24, "time data" should be -- time datum --.

Column 6, line 24, "maximum datum" should be -- maximum data --.

Signed and Sealed this

Third Day of February 1981

[SEAL]

Attest:

RENE D. TEGTMEYER

Attesting Officer    Acting Commissioner of Patents and Trademarks